United States Patent [19]

Schneider

[11] Patent Number: 4,840,391

[45] Date of Patent: Jun. 20, 1989

[54] TRANSPORTATION OF HOSPITAL PATIENTS

[76] Inventor: Karl D. Schneider, 608 Hickory Cir., Canonsburg, Pa. 15317

[21] Appl. No.: 223,266

[22] Filed: Jul. 12, 1988

Related U.S. Application Data

[63] Continuation-in-part of Ser. No. 40,989, Apr. 20, 1987, abandoned.

[51] Int. Cl.$^4$ ............................................. A47C 7/62
[52] U.S. Cl. ............................. 280/304.1; 244/121; 244/231.6
[58] Field of Search ............... 280/289 UC, 242 UC; 297/188, 194, DIG. 4; 248/121, 122, 125, 154, 230, 231.6

[56] References Cited

U.S. PATENT DOCUMENTS

| | | | |
|---|---|---|---|
| 2,678,086 | 5/1954 | Mohr | 248/230 |
| 4,264,085 | 4/1981 | Volin | 280/289 U |
| 4,305,601 | 12/1981 | Berge | 280/289 U |
| 4,511,157 | 4/1985 | Wilt | 297/188 |
| 4,511,158 | 4/1985 | Varga et al. | 297/188 |
| 4,560,128 | 12/1985 | Willeby | 297/188 |
| 4,572,536 | 2/1986 | Doughty | 297/188 |
| 4,600,209 | 7/1986 | Kerr | 280/289 U |

Primary Examiner—Charles A. Marmor
Assistant Examiner—Richard Camby
Attorney, Agent, or Firm—Clifford A. Poff

[57] ABSTRACT

There is provided apparatus which has an elongated, preferably telescopingly adjustable member having at one end thereof a latch engaging the vertically extending pole or standard of a free-wheeling IV mechanism, and a machanism on the opposite end thereof for attaching the same to a vehicle, preferably a wheelchair. In a preferred embodiment, the latch engaging the vertically extending pole or standard has a symmetrical pair of hingedly joined hemicylindrical pieces which are adapted to encircle the pole or standard, one of the pieces being fixedly attached to the elongated member, and there is on one of the two hemicylindrical pieces a locking pin and on the other one of the two hemicylindrical pieces a latch for engaging locking pin. With the aid of such apparatus, a person acting unaided may safely and conveniently transport a passenger-patient connected to IV equipment or apparatus, despite the need to traverse places where the flooring is uneven.

7 Claims, 6 Drawing Sheets

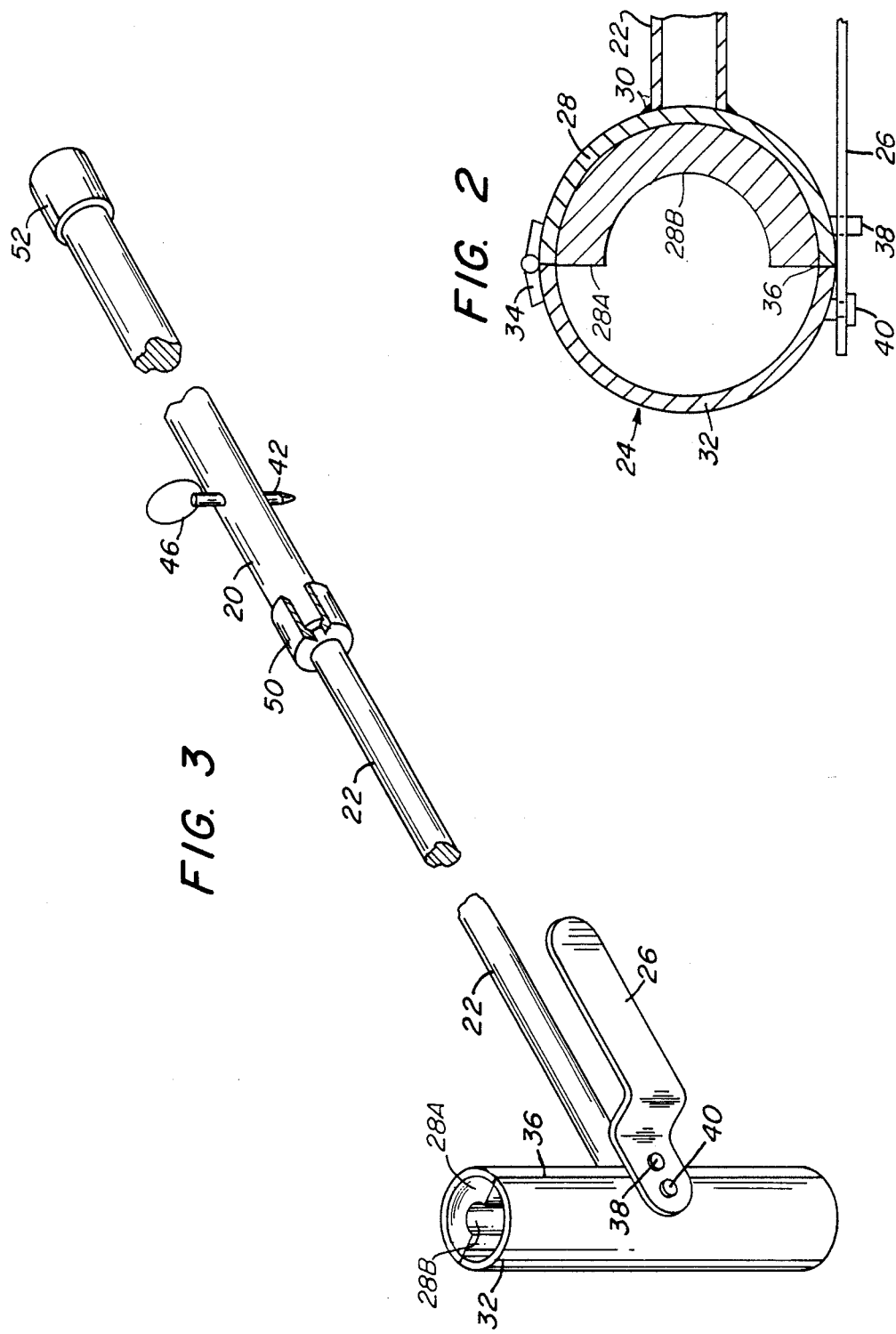

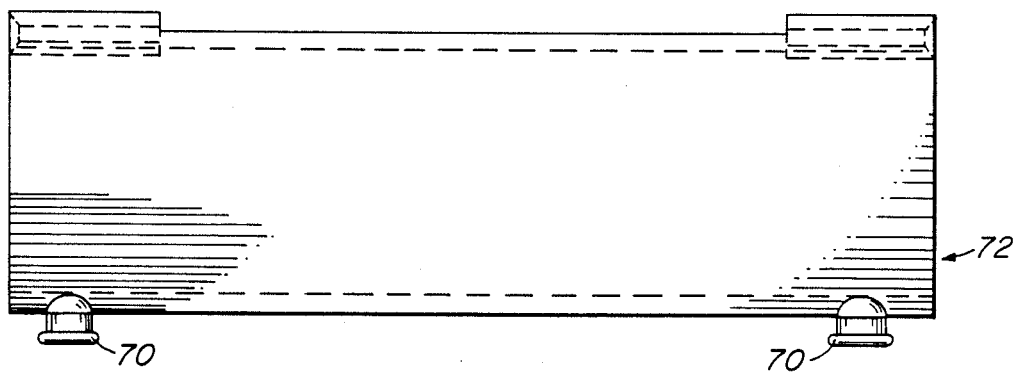
FIG. 7
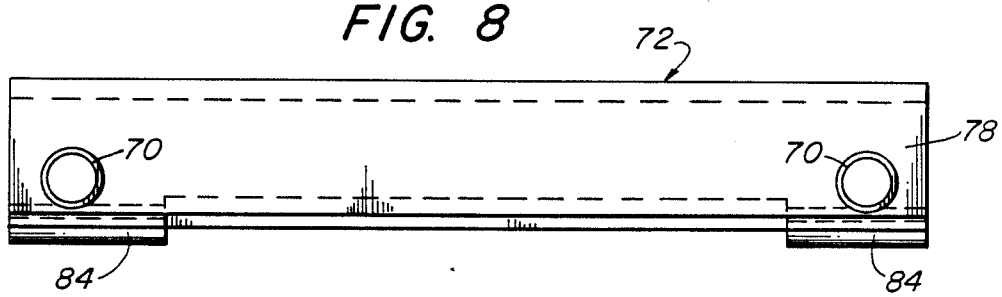
FIG. 8
FIG. 9
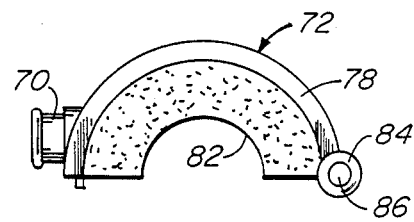
FIG. 11
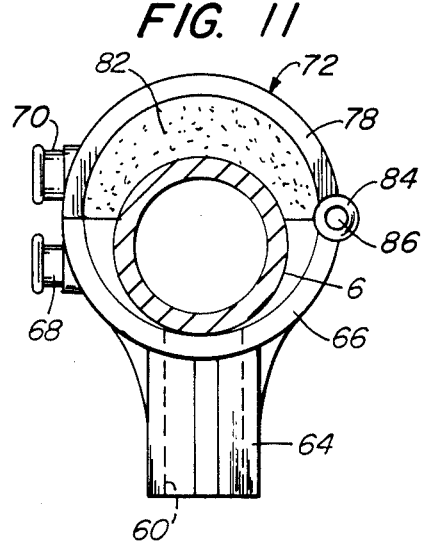
FIG. 10
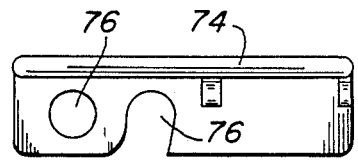

TRANSPORTATION OF HOSPITAL PATIENTS

CROSS-REFERENCE TO RELATED APPLICATIONS

Continuation-in-part of application Ser. No. 040,989, filed Apr. 20, 1987 which is a substitute application for my earlier filed U.S. patent application Ser. No. 749,985, filed July 1, 1985, entitled "TRANSPORTATION OF HOSPITAL PATIENTS".

BACKGROUND OF THE INVENTION

1. Field of the Invention: This invention relates to the transportation of hospital patients, and in particular, to the transportation of patients who are attached to IV (intra-venous) equipment or apparatus of the kind wherein there is an upstanding pole or standard, mounted upon a platform which is borne or supported for free-wheeling motion, as upon casters, with there being attached to the pole or standard at least the source of the fluid being fed intravenously to the patient, and often, additionally, suitable auxiliary equipment such as a volumetric pump. Although patients connected to such equipment usually spend most of their time confined to bed, occasions do arise in which it becomes necessary or advisable to transport them, as by means of a wheelchair or a cart or gurney, to another location. It is not unusual for such trips (for example, to and from the radiology) to involve entering and leaving an elevator. The invention concerns apparatus which facilitates the making up such trips in a safe and convenient manner.

2. Description of the Prior Art: To the best of the inventor's knowledge, the usual practice has been that there is not provided any means which in any way links the free-wheeling IV standard to the vehicle (wheelchair, cart, or gurney) which is being used to transport the patient-passenger having the IV connected to him or her. The person in charge of transporting the patient thus has, as a part of the task, the difficulty of navigating over any uneven places (elevator entries or exits, door jambs, etc.), while at the same time needing somehow to steady and/or guide the IV standard. The IV standard is an item which is, by its nature, of relatively unstable equilibrium and somewhat demanding in its requirements with respect to avoiding having its equilibrium upset. Attention needs to be given to the IV standard at the very times that the guiding of the wheelchair is most likely to call for the use of both hands. For the most part, transporting a patient in a wheelchair through places of the kind mentioned above has been, accordingly, a task that requires the services of a second person, and it is often inconvenient to arrange for such needed help. Accidents and near-accidents occur when the effort is made to transport such a patient wthout such additional help.

It is known, from U.S. Pat. No. 3,709,556, that there is provided a wheelchair which is of such construction that there is provided an upstanding pole or standard which rises from the back of the wheelchair and can serve to support the source of fluid which is being fed to the patient intravenously. Although such equipment may be satisfactory for use with patients who are not in need of intravenous feeding or medication of the kind which requires the use of a volumetric pump, it is not satisfactory for use with patients who do use that kind of equipment, the kind of equipment which is now commonly mounted upon a free-wheeling IV standard which is intended to travel with the patient.

The prior art known to the inventor includes the following references.

The Wilt U.S. Pat. No. 4,511,157, issued Apr. 16, 1985, discloses apparatus for connecting a wheelchair to a portable IV stand which rides on wheels or casters. The teaching of the patent is that there is provided a substantially rigid connection between the two items, namely, one such that if the person pushing the wheelchair, which includes a frame, tilts it backwards, so that its "primary ground engaging wheels rotatably mounted rearwardly on said frame" remain in contact with the ground or floor while its "secondary ground engaging wheels rotatably mounted forwardly on said frame" are raised to be out of contact with the ground or floor, the effect is that the ground engaging wheels or casters of the "portable IV stand are raised from the ground to facilitate passage of said IV stand and said wheelchair over an obstruction on the ground". The Wilt patent also states that "in some applications it might be desirable to utilize elastic or resilient material to produce a rod which can slide inside a sleeve". It holds that kind of structure out as being not preferred. It contains no teaching of the use of a deformable liner member of foam rubber or the like, encircling the IV standard, to grasp it yielding with respect to vertical motion while resisting it or holding it steady against rotary movement.

The prior art includes Lisowski U.S. No. 4,338,875, issued July 13, 1982, "Boats Hardware System" discloses a pair of hingedly jointed pieces 55 and 56, each interiorly of hemicylindrical form. The clamp is secured in the closed position by means of a bolt which passes through the hole in the one piece and into a nut which is embedded in the co-operating piece 55. In the Lisowski patent's structure, the clamping member which has interiorly a pair of hemicylindrical surfaces is also discloses as including a rubber plug member which fits into the hole in the clamp-half. In this respect, the Lisowski clamp member is provided interiorly with a deformable member of rubber which—at least for the purposes of Lisowski in the area of providing hardware for use with boats—affords a clamp with deformable interior member of rubber or the like to increase the grip of the clamp upon the generally cylindrical rail or other member grasped by it. Such a clamp would permit the vertically extending and generally cylindrical pole of an IV stand to be grasped yielding as respects any vertical motion while resisting or preventing rotary motion of the pole.

The prior art also contains U.S. Pat. No. 3,356,330 to Rambelle, entitled "ADJUSTABLE SHORING MEMBER", which discloses a structure that contains, inter alia, a pin means which extends through the openings in tubular member, for locking together the tubular members. Rambelle uses the tubular members which are square rather than rounded, to prevent rotary displacement of one with respect to the other even in the absence of Rambelle's pin means.

The present invention provides a structure inherently more satisfactorily stable and less likely to become upset, in that it tends to keep all of the ground-contacting wheels on the ground, regardless of any irregularities in the floor surface which may be encountered by a particular one or ones of them during travel over said floor surface. The mere encountering of a bump by the caster wheels of the IV standard or by the forward, smaller wheels of the wheelchair is not necessarily an occasion calling for a tilting of the wheelchair back onto its large, rear-mounted wheels, something which probably requires the exertion of attention and effort by someone other than the user-occupant of the wheelchair. The structure of the present invention its more flexible and stable structure and suitable for operation by the unaided effort of the user—occupant, and even in the case that the wheelchair is being propelled by someone else who is in a position to apply force to the rearwardly projecting handles and thereby tilt the wheelchair in order to enable it to clear an obstruction, there is less reason to need to take any such action. The more flexible and stable structure of the present invention

SUMMARY OF THE PRESENT INVENTION

In accordance with the invention, there is provided apparatus which comprises an elongated, telescopingly adjustable member or means, having at one end thereof a means for latchingly engaging the vertically extending pole or standard of a free-wheeling IV mechanism, and means in the vicinity of the opposite end thereof for attaching the same to a vehicle, primarily a wheelchair. In a preferred embodiment, the means for latchingly engaging the vertically extending pole or standard comprises a symmetrical pair of hingedly joined hemicylindrical pieces which are adapted to encircle the pole or standard, one of the pieces being fixedly attached to the elongated member or means, and there is on one of the two hemicylindrical pieces a locking pin and on the other one of the two hemicylindrical pieces a latch for engaging said locking pin; one hemicylindrical piece contains a rubber like material which is squashed against the pole and presses the pole against the other hemicylindrical piece to prevent the pole from slipping or turning about the vertical axis during transport. The telescopingly adjustable member or means of the apparatus is attached to the patient vehicle by means of adjustable screw clamps. With the aid of such aid of such apparatus, a person acting unaided may safely and conveniently transport a passenger-patient connected to IV equipment or apparatus, despite the need to traverse places where the flooring is uneven.

BRIEF DESCRIPTION OF THE DRAWINGS

The present invention will be better understood when read in light of the accompanying drawings in which:

FIG. 2 is a horizontal sectional view of a portion of the apparatus of the invention, illustrating its connection to the IV stand;

FIG. 3 is an isometric view, which illustrates the apparatus of the invention for connection to the IV stand;

FIG. 7 is a bottom view of a second part of the said one form of pin assembly which serves to lock the telescoping horizontal member into a fixed position with respect to the IV standard;

FIG. 8 is a side elevation of the part shown in FIG. 7;

FIG. 9 is an end view of the part shown in FIG. 8;

FIG. 10 is an elevation view of one of two connecting or latching parts which cooperate with the parts shown in FIGS. 4 to 9 to become the said one form of pin assembly which serves the purposes mentioned above;

FIG. 11 is a plane view of an assembly of parts shown in FIGS. 4–10;

DESCRIPTION OF THE PREFERRED EMBODIMENTS

Figure 1:
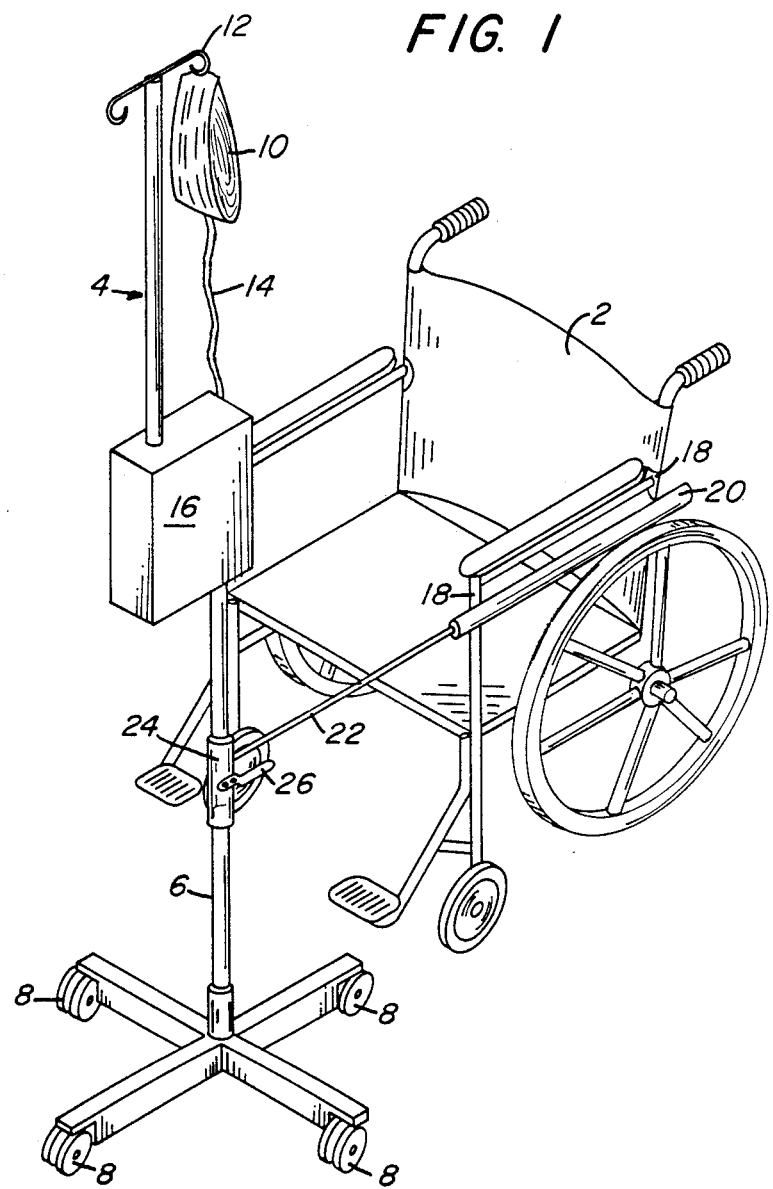
FIG. 1 is a perspective view, showing a wheelchair attached to an IV stand by means of apparatus according to the present invention.

Referring now to the drawings, and in particular, to FIG. 1, there is shown a wheelchair 2 and an IV stand 4, the latter being of the kind which has an upstanding pole or standard 6 and is mounted for free-wheeling movement, supported upon a number of casters 8. Also illustrated are a liquid source 10 suspended from suitable means 12 and connected by a line 14 to a volumetric pump. For simplicity, the means connecting the volumetric pump 16 to the patient are not shown. It will be observed that the wheelchair 2 has, at its sides, a pair of vertically extending tubular members 18.

Figure 1A:
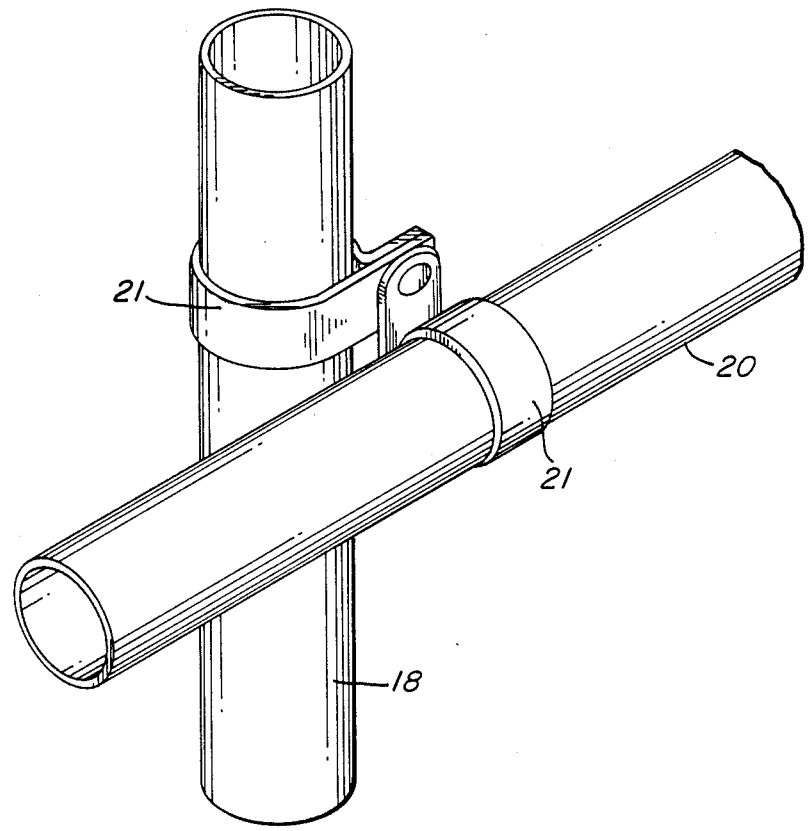
FIG. 1A is a detail exploded view of screw clamp which connects the apparatus to a wheelchair according to the present invention.

The apparatus according to the invention comprises means for connecting the wheelchair 2 to the IV stand 4, and it consists principally of a first tubular member 20 which extends in a generally horizontal direction and is suitably connected to the above-mentioned tubular members 18 such as, for example, by semi-cylindrical screw clamps 21 more clearly shown in the detail view of FIG. 1A, having circumferences similar to that of the outside diameter of the tubular member 20. A second tubular member 22, of somewhat smaller diameter, is telescopingly received within the member 20, and means 24 are provided including a latch 26 which envelopes the pole or standard 6, and the means 24 are suitably connected particularly described hereinbelow.

There is indicated in FIG. 2 the manner in which the smaller-diameter tube 22 may be connected to the means 24. The tube 22 may be joined to a first one hemicylindrical piece 28, as, for example, by welding as indicated at 30. The means 24 for grasping the pole or standard 6 comprises also a second hemicylindrical pieces 32 which forms the second half of a symmetrical pair of such hemicylindrical pieces, these being joined by suitable means, such as a pianotype hinge 34. Diametrically opposite the hinge 34, there is a joint 36 which is formed by means of a pin 38, located on or attached to one of the pieces 28, 32, and the lever 26, which has in one end of it a bore, through which there may be passed a headed pin 40 which is secured to the other one of the pieces 28, 32. Those skilled in the art will appreciate that these pieces 22 and 24 may, if desired, be connected in other different but equivalent ways, without welding. Hemicylinderical piece supports internally thereof a hemicylindrical resilient friction cushion 28A which is provided with a hemicylindrical pocket 28B forming a relief area for the cushion material when squashed against the IV pole. The side of the IV pole opposite the cushion is firmly pressed against the internal surface of hemispherical piece 32 to thereby impart vertical stability to the IV pole and resist twisting of the pole because of the frictional properties of the cushion. It is to be understood that the pole can be driven up or down in means 24 due to change to the floor contour.

Referring now to FIG. 3, there is illustrated how the tube 22 is received telescopingly within the tube 20. And there is shown a pin 42, which is adapted to pass through a bore or opening in the tube 20, as well as through one of a suitable plurality of openings suitably located along the length of the interior tube 22. Those skilled in the art will understand that this permits the tube 22, telescopingly received within the larger tube 20, to be held secure at any desired one of a number of different locations. The pin 42, as illustrated, may have at one end thereof a wire loop 46 which passes through a suitable opening in its upper portion. The larger tube 20 contains bushing material on its inside surface to ease the insertion of the smaller tube 22 and to prevent scarring and nicking tube 22, the bushing retainers being shown at 50 and 52.

Figure 4:
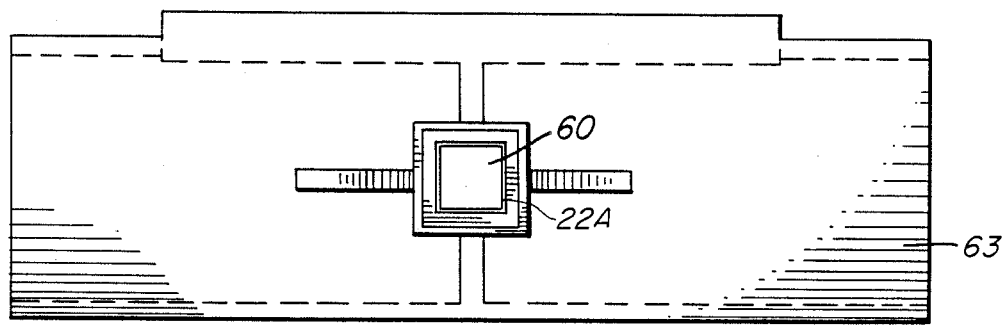
FIG. 4 is a top view of one part of one form of a pin assembly which serves to lock the telescoping horizontal member into a fixed position with respect to the IV standard.
Figure 5:
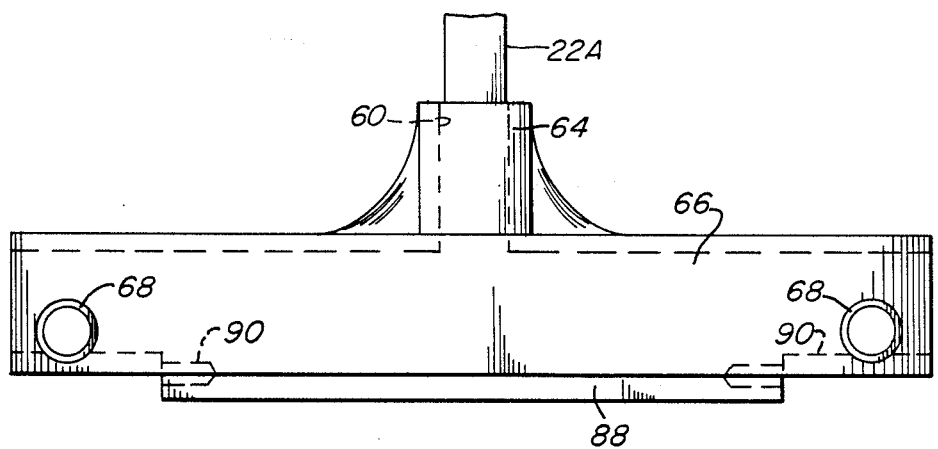
FIG. 5 is an elevation view of one side of the part of FIG. 4.
Figure 6:
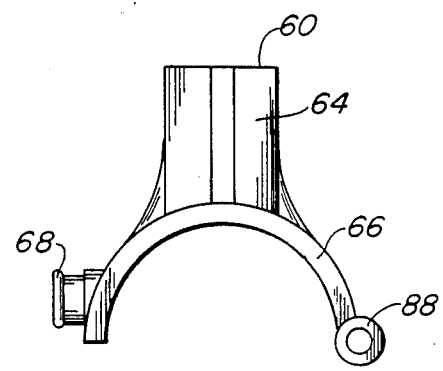
FIG. 6 is an end view of the part of FIG. 5.

Referring now to FIGS. 4 to 10, and more particularly, to FIGS. 4 to 6, these views show, as has been indicated above, the top, elevation, and end views of one part of one form of a pin assembly which serves to connect the telescoping horizontal member 22A to the vertically extending standard 6. The member 22A square in cross section, fits into the corresponding opening 60 in a collar section 64. The collar section receives a tube of a support arm such as tube 22a as described hereinbefore. The collar extends to an elongated hemicylindrical part 66, which bears on its exterior a pair of lugs 68.

There are similar lugs 70 on the cooperating hemicylindrical part 72 shown in FIGS. 7, 8, and 9. There are two latch pieces 74, shown in FIG. 10, that have various openings 76, for joining a lug 68 to a lug 70 when the parts 66 and 72 have been joined hingedly together, in the manner more particularly indicated hereinbelow. The hemicylindrical part 78 of the piece 72 is lined interiorly with flexible material such as sponge rubber, foam rubber, or polyurethane foam, as at 80. As can be seen from FIG. 11, the material 80 is squashed against the hemicylindrical side of the IV pole which presses pole which presses the opposite hemicylindrical side of the pole against the internal wall of hemicylindrical part 66. The frictional property of material 80 and the pressure generated by the squashing thereof, prevents spinning of the pole but allows the pole to move longitudinally. Such longitudinal movement is guided by the internal wall of the hemicylindrical part 66 and resisted by the squashed material 80. The longitudinal movement occurs because the IV pole is displaced vertically as changes to elevation occurs to the pole before such changes affect the wheel chair or cart.

There are on the piece 72 certain protuberances 84 which, as can be seen in FIG. 9, are of generally circular cross section and have therein a central cavity or bore 86, and these protuberances 88 are, in the assembly of this part of the apparatus, aligned and hingedly joined with the similar protuberance 88 on the part 66 by pins extending through the openings in the protuberances 84, 88 and into the aligned cavity or bore 90 (see FIG. 5). From what has been said, the manner of assembling and latching these parts, to effect a joining of member 22 to standard 6 in such a manner as to permit the standard 6 to slide vertically while being held against rotary motion, will be apparent to those skilled in the art.

Figure 12:
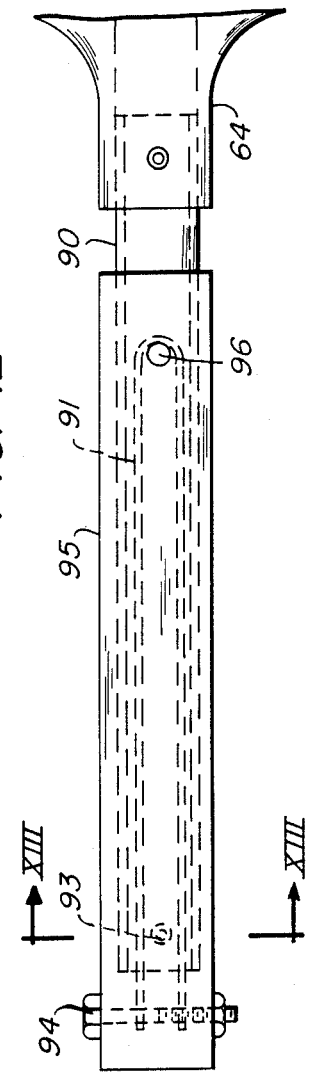
FIG. 12 is a plan view of a preferred embodiment of a telescopic arm forming part of the present invention.
Figure 14:
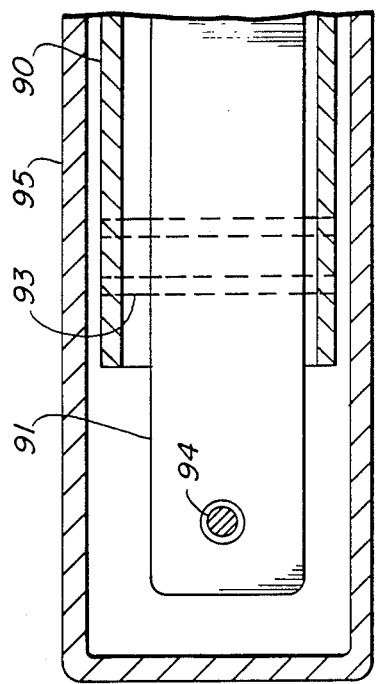
FIG. 14 is a sectional view taken along lines XIV—XIV of FIG. 13.
Figure 13:
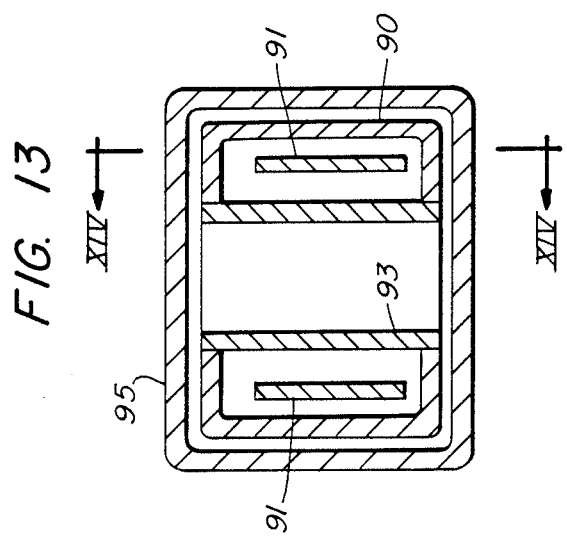
FIG. 13 is a sectional view taken along line XII—XII of FIG. 12.

Turning now to FIGS. 12-14, there is illustrated preferred embodiment of telescoping arm by which an IV pole assembly can be releasably coupled to a wheeled vehicle, such as a wheel chair. In this embodiment, the collar 64 has a square internal opening 60 into which there is received a first square tube 90 which includes a hollow internal area in which a flexible metal band 91 extends. The band 91 is arranged so that opposite end portions protrude from the end of the tube which is opposite to collar 64. The reverse bend of the metal band is, however, closely spaced from the tube 64. The end portion of tube 90 from which the terminal ends of the flexible band extend, is provided with an anchor bushing 93 which, as can be seen from FIG. 13 is arranged so that the end portions of the flexible band 91 extend along opposite sides of the anchor. The flexible band are secured by a fastener 94 to an end portion of a second tube 95 which has an internal area sufficient to accommodate and slide along the outer surface of tube 90. As tube 90 is drawn in a right-hand direction as one views FIG. 12, the anchor bushing 93 advances toward the reverse bend of flexible band 91 until the reverse bend in the band contacts the anchor bushing 93. When this occurs there is appropriately provided an opening 96 in tube 95 which aligns with the internal opening in anchor bushing 93. This aligned relation permits the insertion of the an anchor pin interlocking the two tubes 90 and 95 at their telescopically extended position. The band serves as an automatic positioned device so that the tube 90 may be quickly drawn from its nested relation in tube 95 for securing in an extended position and thereby presenting the part 93 for engagement with an IV pole in a manner described hereinbefore.

While the present invention has been described in accordance with the preferred embodiments of the various figures, it is to be understood that other similar embodiments may be used or modifications and additions may be made to the described embodiment for performing the same functions of the present invention without deviating therefrom. Therefore, the present invention should not be limited to any single embodiment, but rather construed in breadth and scope in accordance with the recitation of the appended claims.

I claim as my invention:

1. Attachment apparatus for joining a patient carrying wheeled vehicle to an intravenous pole assigned having an upstanding elongated IV pole mounted upon a wheeled base, said attachment apparatus comprising an elongated arm including two tubes telescopically received one within the other;
   an elongated tubular housing formed by two arcuate segments connected by a hinge, one of said acruate segment being fixedly connected to an end of one of said tubes;
   latch means releasably connecting said two arcuate segments into said tubular housing; and
   stop means located within said tubes for limiting the extent of extension of said tubes, said tubes means including a positioning means anchored to one of said tubes and a flexible member having terminal end portions secured to the other one of said tubes.

2. The attachment apparatus according to claim 1 wherein said latch means includes post members at opposite end portions of the elongated length of said tubular housing, and latch plates pivotally supported by an arcuate segment of said housing opposite the arcuate segment having said post members for locking engagement with the post members.

3. The attachment apparatus according to claim 1 further including means for interlocking said tubes in their extending position.

4. The attachment apparatus according to claim 1 wherein said stop means includes a flexible metal band having terminal end portions secured by a fastener to one of said tubes.

5. The attachment apparatus according to claim 4 wherein said flexible band member is engageable with an anchor pin supported by the other of said tubes at a position determining the extended telescopic position of one tube relative to the other.

6. Apparatus as defined in claim 5, wherein said friction means includes hemicylindrical resilient member.

7. The apparatus according to claim 1, wherein said elongated tubular housing extends along a length of the pole for guided longitudinal movement by the pole and wherein said apparatus further includes means supported by one of the said hemicylindrical pieces for squashing against said pole to thereby press the opposite side of said pole against a hemicylindrical piece to restrain said pole against rotary movement with respect to said hemicylindrical pieces.

* * * * *